US009480421B2

(12) United States Patent
Stafford

(10) Patent No.: US 9,480,421 B2
(45) Date of Patent: *Nov. 1, 2016

(54) INTEGRATED INTRODUCER AND TRANSMITTER ASSEMBLY AND METHODS OF USE

(71) Applicant: Abbott Diabetes Care Inc., Alameda, CA (US)

(72) Inventor: Gary Ashley Stafford, Hayward, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 13/970,397

(22) Filed: Aug. 19, 2013

(65) Prior Publication Data

US 2013/0338463 A1 Dec. 19, 2013

Related U.S. Application Data

(63) Continuation of application No. 11/240,259, filed on Sep. 30, 2005, now Pat. No. 8,512,243.

(51) Int. Cl.
*A61B 5/145* (2006.01)
*A61B 5/00* (2006.01)

(52) U.S. Cl.
CPC ......... *A61B 5/14503* (2013.01); *A61B 5/1451* (2013.01); *A61B 5/14532* (2013.01); *A61B 5/14542* (2013.01); *A61B 5/14546* (2013.01); *A61B 5/6849* (2013.01); *A61B 5/0002* (2013.01); *A61B 2560/063* (2013.01)

(58) Field of Classification Search
CPC ............ A61B 5/14503; A61B 5/0002; A61B 5/14532; A61B 5/6849; A61B 5/1451; A61B 5/14542; A61B 5/14546; A61B 2560/063
USPC .................. 600/345–366, 373; 606/181–189
See application file for complete search history.

(56) References Cited

U.S. PATENT DOCUMENTS

| | | | |
|---|---|---|---|
| 3,123,790 A | 3/1964 | Tyler |
| 3,211,001 A | 10/1965 | Petit |
| 3,260,656 A | 7/1966 | Ross, Jr. |
| 3,581,062 A | 5/1971 | Aston |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |

(Continued)

FOREIGN PATENT DOCUMENTS

| | | |
|---|---|---|
| CA | 2291105 | 12/1998 |
| DE | 4401400 | 7/1995 |

(Continued)

OTHER PUBLICATIONS

Alcock, S. J., et al., "Continuous Analyte Monitoring to Aid Clinical Practice", *IEEE Engineering in Medicine and Biology Magazine*, 1994, pp. 319-325.

(Continued)

*Primary Examiner* — Navin Natnithithadha
(74) *Attorney, Agent, or Firm* — One LLP

(57) ABSTRACT

Method and apparatus for inserting at least a portion of a sensor into a patient is provided.

20 Claims, 5 Drawing Sheets

(56) References Cited

U.S. PATENT DOCUMENTS

| | | |
|---|---|---|
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardiern |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka et al. |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guilbeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |

(56) References Cited

U.S. PATENT DOCUMENTS

| | | |
|---|---|---|
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Metcalf et al. |
| 5,545,191 A | 8/1996 | Mann et al. |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |
| 5,899,855 A | 5/1999 | Brown |

(56) References Cited

U.S. PATENT DOCUMENTS

| | | |
|---|---|---|
| 5,924,979 A | 7/1999 | Sedlow et al. |
| 5,925,021 A | 7/1999 | Castellano et al. |
| 5,931,868 A | 8/1999 | Gross et al. |
| 5,938,679 A | 8/1999 | Freeman et al. |
| 5,948,006 A | 9/1999 | Mann |
| 5,951,521 A | 9/1999 | Mastrototaro et al. |
| 5,951,582 A | 9/1999 | Thorne et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,302,866 B1 | 10/2001 | Marggi |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,433,743 B1 | 8/2002 | Massey et al. |
| 6,435,017 B1 | 8/2002 | Nowicki, Jr. et al. |
| 6,437,679 B1 | 8/2002 | Roques |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,551,496 B1 | 4/2003 | Moles et al. |
| 6,554,795 B2 | 4/2003 | Lam et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,988 B2 | 1/2005 | Leong et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |

(56) References Cited

U.S. PATENT DOCUMENTS

| | | |
|---|---|---|
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,682,338 B2 | 3/2010 | Griffin |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,766,829 B2 | 8/2010 | Sloan et al. |
| 7,822,454 B1 | 10/2010 | Alden et al. |
| 8,512,243 B2 * | 8/2013 | Stafford ............ A61B 5/14532 600/309 |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0165462 A1 | 11/2002 | Westbrook et al. |
| 2002/0169369 A1 | 11/2002 | Ward et al. |
| 2002/0198444 A1 | 12/2002 | Ughigaki et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0072357 A1 | 4/2004 | Stiene et al. |
| 2004/0096959 A1 | 5/2004 | Sliene et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |

(56) References Cited

U.S. PATENT DOCUMENTS

| | | |
|---|---|---|
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfield et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096520 A1 | 5/2005 | Maekawa et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0267327 A1 | 12/2005 | Iizuka et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1* | 4/2007 | Stafford .......... A61B 5/14532 600/347 |
| 2007/0095661 A1 | 5/2007 | Wang et al. |
| 2007/0106135 A1 | 5/2007 | Sloan et al. |
| 2007/0110124 A1 | 5/2007 | Shiraki et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0099332 A1 | 5/2008 | Scott et al. |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0161664 A1 | 7/2008 | Mastrototaro et al. |

(56) References Cited

U.S. PATENT DOCUMENTS

| | | |
|---|---|---|
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262330 A1 | 10/2008 | Reynolds et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0259202 A1 | 10/2009 | Leeflang et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gyrn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0174157 A1 | 7/2010 | Brister et al. |
| 2010/0174158 A1 | 7/2010 | Kamath et al. |
| 2010/0174163 A1 | 7/2010 | Brister et al. |

(56) References Cited

U.S. PATENT DOCUMENTS

| | | |
|---|---|---|
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gyrn et al. |
| 2010/0212583 A1 | 8/2010 | Brister et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0288574 A1 | 11/2011 | Curry et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0296327 A1 | 11/2012 | Hutchins et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2003-527138 | 9/2003 |
| JP | 2004-520103 | 7/2004 |
| JP | 2004-520898 | 7/2004 |
| JP | 2006-517804 | 8/2006 |
| WO | WO-96/39977 | 5/1996 |
| WO | WO-96/25089 | 8/1996 |
| WO | WO-96/35370 | 11/1996 |
| WO | WO-97/21457 | 6/1997 |
| WO | WO-98/35053 | 8/1998 |
| WO | WO-98/56293 | 12/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/028784 | 4/2003 |
| WO | WO-03/073936 | 9/2003 |
| WO | WO-03/076893 | 9/2003 |
| WO | WO-03/082091 | 10/2003 |

(56) References Cited

FOREIGN PATENT DOCUMENTS

| WO | WO-2004/054445 | 7/2004 |
|---|---|---|
| WO | WO-2004/060436 | 7/2004 |
| WO | WO-2004/061420 | 7/2004 |
| WO | WO-2005/084534 | 9/2005 |
| WO | WO-2005/089103 | 9/2005 |
| WO | WO-2006/042811 | 4/2006 |
| WO | WO-2006/108809 | 10/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/120363 | 10/2007 |
| WO | WO-2007/140783 | 12/2007 |
| WO | WO-2007/143225 | 12/2007 |
| WO | WO-2008/031106 | 3/2008 |
| WO | WO-2008/031110 | 3/2008 |
| WO | WO-2008/039944 | 4/2008 |
| WO | WO-2008/051920 | 5/2008 |
| WO | WO-2008/051924 | 5/2008 |
| WO | WO-2008/065646 | 6/2008 |
| WO | WO-2008/103620 | 8/2008 |
| WO | WO-2008/133702 | 11/2008 |
| WO | WO-2008/150917 | 12/2008 |
| WO | WO-2009/062675 | 5/2009 |
| WO | WO-2010/112521 | 10/2010 |
| WO | WO-2011/002815 | 1/2011 |

OTHER PUBLICATIONS

Armour, J. C., et al., "Application of Chronic Intravascular Blood Glucose Sensor in Dogs", *Diabetes*, vol. 39, 1990, pp. 1519-1526.
Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.
Bennion, N., et al., "Alternate Site Glucose Testing: A Technology Crossover Design", *Diabetes & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Blank, T. B., et al., "Clinical Results From a Non-Invasive Blood Glucose Monitor", Optical and Diagnostics and Sensing of Biological Fluids and Glucose Cholesterol Monitoring II, *Proceedings of SPIE*, vol. 4624, 2002, pp. 1-10.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Brooks, S. L., et al., "Development of an On-Line Glucose Sensor for Fermentation Monitoring", *Biosensors*, vol. 3, 1987/1988, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Csoregi, E., et al., "Design and Optimization of a Selective Subcutaneously Implantable Glucose Electrode Based on 1995, 'Wired' Glucose Oxidase", *Analytical Chemistry*, vol. 67, No. 7, pp. 1240-1244.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Glucose Change", *Abbott Diabetes Care, Inc. Freestyle Navigator Blood During Periods of Rapid Continuous Glucose Monitor Pamphlet*, 2004.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gunasingham, et al., "Electrochemically Modulated Optrode for Glucose", *Biosensors & Bioelectronics*, vol. 7, 1992, pp. 353-359.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Heller, A., "Electrical Connection Enzyme Redox Centers to Electrodes", *Journal of Physical Chemistry*, vol. 96, No. 9, 1990, pp. 3579-3587.
Ikeda, T., et al., "Artificial Pancreas—Investigation of the Stability of Glucose Sensors Using a Telemetry System" (English language translation of abstract), *Jpn. J. Artif. Organs*, vol. 19, No. 2, 1990, pp. 889-892.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Maidan, R., et al., "Elimination of Electrooxidizable Interferant-Produced Currents in Amperometric Biosensors", *Analytical Chemistry*, vol. 64, No. 23, 1992, pp. 2889-2896.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
Mastrototaro, J. J., et al., "An Electroenzymatic Glucose Sensor Fabricated on a Flexible Substrate", *Sensors and Actuators B*, vol. 5, 1991, pp. 139-144.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Minimed Technologies, "Tape Tips and Other Infusion Site Information", 1995.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.
Pickup, J., et al., "Implantable Glucose Sensors: Choosing the Appropriate Sensing Strategy", *Biosensors*, vol. 3, 1987/1988, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

(56) References Cited

OTHER PUBLICATIONS

Poitout, V., et al., "In Vitro and In Vivo Evaluation in Dogs of a Miniaturized Glucose Sensor", *ASAIO Transactions*, vol. 37, No. 3, 1991, pp. M298-M300.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64 No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Roe, J. N., et al., "Bloodless Carrier Measurements", *Critical Review in Therapeuti Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29 No. 13, 1996, pp. 2289-2308.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

Ye, L., et al., "High Current Density 'Wired' Quinoprotein Glucose Dehydrogenase Electrode", *Analytical Chemistry*, vol. 65, No. 3, 1993, pp. 238-241.

European Patent Application No. EP-06804122.7, Decision to Refuse the Application mailed Feb. 25, 2013.

European Patent Application No. EP-06804122.7, Extended European Search Report mailed Sep. 28, 2009.

European Patent Application No. EP-06804122.7, Official Letter mailed Jan. 25, 2011.

European Patent Application No. EP-06804122.7, Official Letter mailed Nov. 30, 2011.

European Patent Application No. EP-07842180.7, Examination Report mailed Oct. 23, 2012.

European Patent Application No. EP-07842180.7, Extended Search Report mailed Sep. 28, 2009.

European Patent Application No. EP-07842180.7, Official Letter mailed Dec. 14, 2011.

European Patent Application No. EP-07842180.7, Second Office Action mailed Feb. 23, 2011.

PCT Application No. PCT/US2006/037312, International Preliminary Report on Patentability and Written Opinion of the International Searching Authority mailed Apr. 11, 2008.

PCT Application No. PCT/US2006/037312, International Search Report and Written Opinion of the International Searching Authority mailed Apr. 17, 2007.

PCT Application No. PCT/US2007/078073, International Search Report and Written Opinion of the International Searching Authority mailed Apr. 11, 2008.

U.S. Appl. No. 11/240,259, Notice of Allowance mailed Jun. 3, 2013.

U.S. Appl. No. 11/240,259, Office Action mailed Jun. 5, 2009.
U.S. Appl. No. 11/240,259, Office Action mailed Nov. 30, 2009.
U.S. Appl. No. 11/240,259, Office Action mailed Nov. 29, 2007.
U.S. Appl. No. 11/240,259, Office Action mailed Oct. 6, 2008.
U.S. Appl. No. 11/530,473, Office Action mailed Dec. 11, 2009.
U.S. Appl. No. 11/530,473, Office Action mailed Jan. 10, 2008.
U.S. Appl. No. 11/530,473, Office Action mailed Jun. 25, 2010.
U.S. Appl. No. 11/530,473, Office Action mailed May 14, 2009.
U.S. Appl. No. 11/530,473, Office Action mailed Oct. 6, 2008.

U.S. Patent Reexamination Application No. 90/008,172, Request for Reexamination of U.S. Pat. No. 6,990,366, filed Aug. 16, 2006.

U.S. Patent Reexamination Application No. 90/008,457, Notice of Intent to Issue Reexamination Certificate mailed Mar. 13, 2008.

U.S. Patent Reexamination Application No. 90/008,457, Order Granting Request for Reexamination mailed Feb. 23, 2007.

U.S. Patent Reexamination Application No. 90/008,457, Request for Reexamination of U.S. Pat. No. 6,990,366, filed Jan. 23, 2007.

U.S. Patent Reexamination Application No. 90/009,104 & 90/009,328, Notice of Intent to Issue Reexamination Certificate mailed Nov. 20, 2009.

U.S. Patent Reexamination Application No. 90/009,104 & 90/009,328, Office Action mailed Aug. 4, 2009.

U.S. Patent Reexamination Application No. 90/009,104 & 90/009,328, Office Action mailed Sep. 30, 2009.

U.S. Patent Reexamination Application No. 90/009,104, Office Action mailed Oct. 16, 2008.

U.S. Patent Reexamination Application No. 90/009,104, Order Granting Request for Reexamination mailed Jun. 5, 2008.

U.S. Patent Reexamination Application No. 90/009,104, Request for Reexamination of U.S. Pat. No. 6,990,366 filed Apr. 8, 2008.

U.S. Patent Reexamination Application No. 90/009,328, Order Granting Request for Reexamination mailed Dec. 9, 2008.

U.S. Patent Reexamination Application No. 90/009,328, Request for Reexamination of U.S. Pat. No. 6,990,366 filed Nov. 10, 2008.

(56) References Cited

OTHER PUBLICATIONS

U.S. Patent Reexamination Application No. 90/010,791, Notice of Intent to Issue Reexamination Certificate mailed May 17, 2011.
U.S. Patent Reexamination Application No. 90/010,791, Office Action mailed Dec. 17, 2010.
U.S. Patent Reexamination Application No. 90/010,791, Office Action mailed May 28, 2010.
U.S. Patent Reexamination Application No. 90/010,791, Order Granting Request for Reexamination mailed Feb. 22, 2010.
U.S. Patent Reexamination Application No. 90/010,791, Request for Reexamination of U.S. Pat. No. 6,990,366 filed Dec. 22, 2009.
U.S. Patent Reexamination Application No. 90/011,730, Notice of Intent to Issue Reexam Certificate for U.S. Pat. No. 6,990,366 mailed Apr. 5, 2012.
U.S. Patent Reexamination Application No. 90/011,730, Office Action mailed Jan. 11, 2012.
U.S. Patent Reexamination Application No. 90/011,730, Order Granting Request for Reexamination of U.S. Pat. No. 6,990,366 mailed Aug. 24, 2011.
U.S. Patent Reexamination Application No. 90/011,730, Request for Reexamination of U.S. Pat. No. 6,990,366 filed Jun. 3, 2011.
U.S. Patent Reexamination Application No. 95/002,113, Order Denying Request for Reexamination of U.S. Pat. No. 6,990,366 mailed Nov. 13, 2012.
U.S. Patent Reexamination Application No. 95/002,113, Petition for Review of the Order Denying Request Reexamination of U.S. Pat. No. 6,990,366 mailed Dec. 13, 2012.
U.S. Patent Reexamination Application No. 95/002,113, Request for Reexamination of U.S. Pat. No. 6,990,366 filed Aug. 30, 2012.
U.S. Patent Reexamination Application No. 95/002,162, Order Denying Request for Reexamination of U.S. Pat. No. 8,175,673 mailed Nov. 13, 2012.
U.S. Patent Reexamination Application No. 95/002,162, Petition for Review of the Order Denying Request Reexamination of U.S. Pat. No. 8,175,673 mailed Dec. 13, 2012.
U.S. Patent Reexamination Application No. 95/002,162, Request for Reexamination of U.S. Pat. No. 8,175,673 filed Sep. 7, 2012.

\* cited by examiner

INTEGRATED INTRODUCER AND TRANSMITTER ASSEMBLY AND METHODS OF USE

RELATED APPLICATIONS

The present application is a continuation of U.S. patent application Ser. No. 11/240,259 filed Sep. 30, 2005, now U.S. Pat. No. 8,512,243, the disclosure of which is incorporated herein by reference for all purposes.

BACKGROUND

Continuous glucose monitoring systems generally include a sensor such as a subcutaneous analyte sensor, at least a portion of which is inserted under the skin for fluid contact with interstitial fluid, for detecting analyte levels such as glucose levels, a transmitter (such as an RF transmitter) in communication with the sensor and configured to receive the sensor signals and to transmit them to a corresponding receiver unit by for example, using RF data transmission protocol. The receiver may be operatively coupled to a glucose monitor that performs glucose related calculations and data analysis.

The transmitter is in signal communication with the sensor. Generally, the sensor is configured to detect and measure the glucose levels of the patient over a predetermined period of time, and the transmitter is configured to transmit data corresponding to or associated with the measured glucose levels over the predetermined period of time for further analysis. To initially deploy the sensor so that the sensor contacts and electrodes are in fluid contact with the patient's interstitial fluids, a separate deployment mechanism such as a sensor inserter or introducer is used. More specifically, the introducer includes a sharp needle shaped inserter that is configured to pierce through the skin of the patient and substantially concurrently guide the sensor through the patient's skin so as to place at least a portion of the sensor in fluid contact with the target biological fluid of the patient.

The sharp inserter is typically used only during the sensor insertion process, and once the sensor is properly and accurately positioned, the inserter and the introducer are discarded. This requires a level of care as the inserter is sharp and may damage other parts of the patient's skin if not properly discarded. Further, since the tip of the inserter has come into fluid contact with the patient's biological fluids, it is important to take particular precautions in the handling of the sharp inserter.

Further, to minimize data errors in the continuous or semi-continuous monitoring system, it is important to properly insert the sensor through the patient's skin and securely retain the sensor during the time that the sensor is configured to detect analyte levels. In addition to accurate positioning of the sensor through the skin of the patient, it is important to minimize the level of pain associated with the insertion of the sensor through the patient's skin. Additionally, for the period of continuous or semi-continuous monitoring which can include, for example, 3 days, 5 days or 7 days, it is important to have the transmitter in proper contact with the analyte sensor so as to minimize the potential errors in the monitored data.

In view of the foregoing, it would be desirable to have method and apparatus which provides for simple handling of the sensor introducer during sensor deployment and also after the sensor deployment. More specifically, it would be desirable to have method and apparatus that minimizes the potential physical contact with the inserter mechanism and the patient to minimize the potential for disseminating the biological fluids that have come into contact with the inserter, and also, that provides for an easy to use sensor insertion mechanism that minimizes the pain to the patient.

SUMMARY

In one embodiment, there is provided a method and apparatus for providing an integrated sensor introducer mechanism and transmitter unit for use in continuous or semi-continuous monitoring systems such as glucose monitoring systems which includes a disposable sensor introducer provided within the integrated sensor/transmitter assembly and which is retained within the assembly during the time period of the sensor in active mode.

More specifically, in one embodiment of the present invention, there is provided an integrated sensor introducer mechanism which may be triggered by a single depression or activation of a switch to deploy the sharp sensor introducer through the skin of the patient. The single depression trigger mechanism is configured to return to its original position upon firing the sensor and the introducer, so that the sharp sensor introducer is removed from the patient after placing the sensor in the patient.

In this manner, the patient is not required to handle the cumbersome and potentially dangerous and sharp sensor introducer microneedle, for example. In this manner, a convenient, simple and sanitary sensor insertion and analyte monitoring system is provided.

DETAILED DESCRIPTION

Figure 1A:
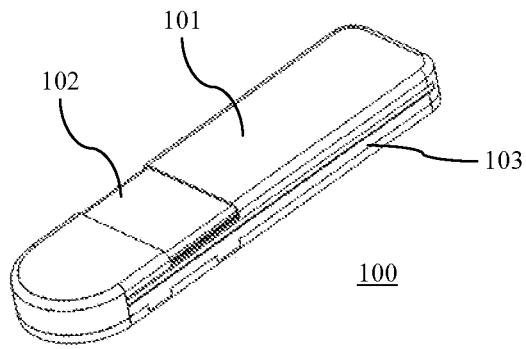
FIG. 1A illustrates a perspective view of the overall assembly including integrated introducer and transmitter coupled to the transmitter mount with the switch cover in a closed position in accordance with one embodiment of the present invention.
Figure 1B:
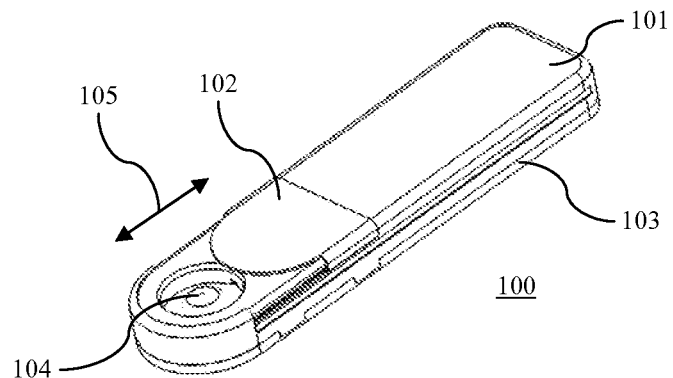
FIG. 1B illustrates a perspective view of the overall assembly including integrated introducer and transmitter coupled to the transmitter mount with the switch cover in an open position in accordance with one embodiment of the present invention.

FIG. 1A illustrates a perspective view of the overall assembly including integrated introducer and transmitter coupled to the transmitter mount with the switch cover in a closed position in accordance with one embodiment of the present invention, and FIG. 1B illustrates a perspective view of the overall assembly including integrated introducer and transmitter coupled to the transmitter mount with the switch cover in an open position in accordance with one embodiment of the present invention. Referring to FIGS. 1A-1B, integrated sensor introducer and transmitter assembly 100 in one embodiment of the present invention includes a transmitter unit 101, a transmitter unit opening portion 102, and transmitter mount base portion 103. As shown, the transmitter unit 101 is configured to physically couple to the transmitter mount base portion 103 so as to provide an integrated assembly. The transmitter mount base portion 103 is configured to be placed on the skin of a patient, and as will be discussed in further detail, and includes a sensor introducer and the sensor pre-assembled therein.

Referring to FIGS. 1A-1B, the transmitter unit opening portion 102 is configured in one embodiment to be slidably displaced between an open position and a closed position, along the directional arrow 105. As can be seen, when the transmitter unit opening portion 102 is in the open position, a sensor introducer trigger mechanism 104 is exposed to the patient. More specifically, the patient is able to slidably move the transmitter unit opening portion 102 between the open position and the closed position to operate the sensor introducer trigger mechanism 104, and upon successfully deploying the sensor transcutaneously to the desired position, the patient may place the transmitter unit opening portion 102 in the closed position so as to provide cover and protection to the sensor introducer trigger mechanism 104, and also, to avoid potential inadvertent interaction with the sensor introducer trigger mechanism 104. Within the scope of the present invention, the sensor introducer trigger mechanism 104 may include a plug or stopper with a latch mechanism.

Referring back to FIGS. 1A-1B, while the transmitter unit opening portion 102 is shown with a slidable movement so as to be displaced between the open position and the closed position, within the scope of the present invention, the transmitter unit opening portion 102 may include other types of mechanisms to open and close the area exposing the sensor introducer trigger mechanism 104. For example, the transmitter unit opening portion 102 may include a hinge portion pivotally mounted to the transmitter unit 101 so that the transmitter unit opening portion 102 may pivotally move to expose and to close the sensor introducer trigger mechanism.

Additionally, a latch mechanism may also be provided so as to securely place the transmitter unit opening portion 102 in a closed and latched position so as to avoid potential inadvertent exposure of the sensor introducer trigger mechanism 104. Within the scope of the present invention, the latch mechanism may include a Velcro type fastener, a button type latching mechanism, a tongue and groove type latch mechanism, a snap, a détente, a hook, or any other type of latching mechanism that would securely place the transmitter unit opening portion 102 in the closed position in the event of inadvertent application of pressure thereto.

Figure 2:
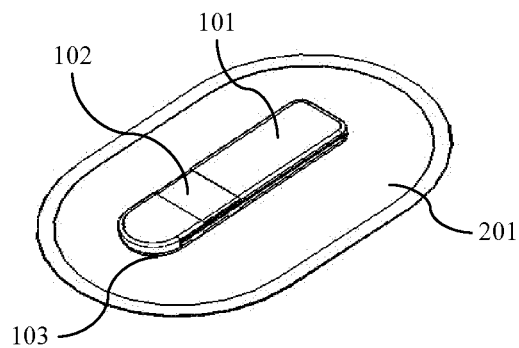
FIG. 2 illustrates a perspective view of the overall assembly including integrated introducer and transmitter coupled to the transmitter mount with the switch cover in a closed position provided on an adhesive patch in accordance with one embodiment of the present invention.

FIG. 2 illustrates a perspective view of the overall assembly including integrated introducer and transmitter coupled to the transmitter mount with the switch cover in a closed position provided on an adhesive patch in accordance with one embodiment of the present invention. Referring to FIG. 2, there is shown an adhesive patch 201 that is configured to receive the transmitter unit base portion 103 on its upper surface, while the lower surface is provided with an adhesive material, and where the lower surface is configured to be securely attached to the skin of the patient, thus effectively providing a firm and secure mounting of the integrated sensor introducer and transmitter assembly 100. As shown, the adhesive patch 201 in one embodiment of the present invention is substantially flexible and configured to substantially follow the contour of the patient's skin where the integrated sensor introducer and transmitter assembly 100 is to be placed for the predetermined period of time that the patient will be wearing the assembly 100 (for example, 3 days, 5 days, 7 days and so on). In this manner, comfort can be provided to the patient while not substantially hindering the patient's daily activities.

Figure 3A:
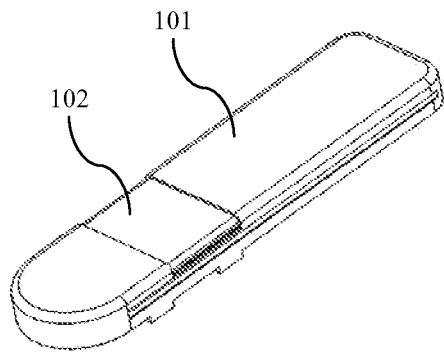
FIGS. 3A and 3B illustrate the open and closed positions, respectively, of the transmitter unit opening portion on the transmitter unit housing in accordance with one embodiment of the present invention.
Figure 3B:
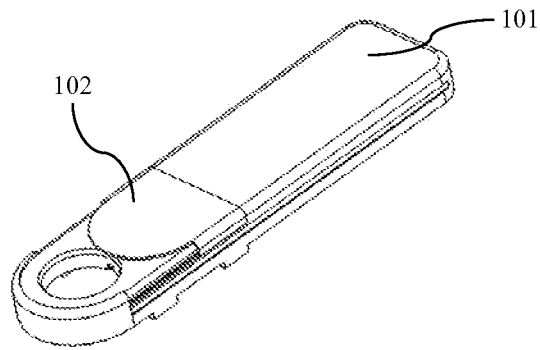
Figure 4:
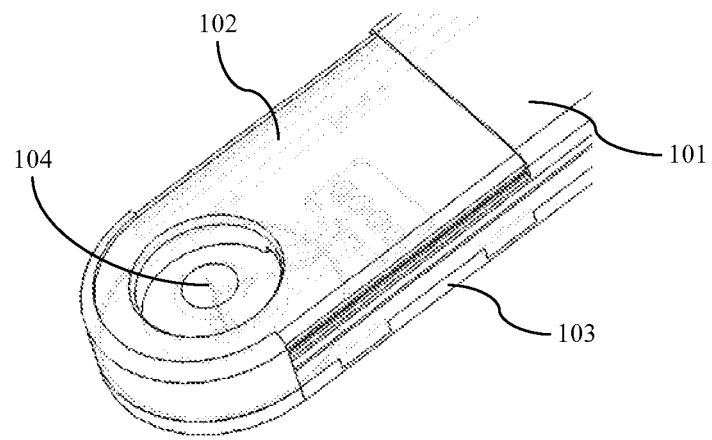
FIG. 4 illustrates a close up perspective view of the switch opening in the open position exposing the sensor introducer trigger mechanism and mounted on the transmitter unit base portion in accordance with one embodiment of the present invention.

FIGS. 3A and 3B illustrate the open and closed positions, respectively, of the transmitter unit opening portion on the transmitter unit housing, and FIG. 4 illustrates a close-up, perspective view of the switch opening in the open position exposing the sensor introducer trigger mechanism and mounted on the transmitter unit base portion in accordance with one embodiment of the present invention. Referring to FIGS. 3A-3B and 4, it can be seen that the sensor introducer trigger mechanism 104 is positioned substantially within the housing of the integrated sensor introducer and transmitter assembly 100, shown in one embodiment as including the transmitter unit 101 coupled with the transmitter unit base portion 102.

Moreover, while the transmitter unit 101 is provided with a substantially circular opening corresponding to the position of the sensor introducer trigger mechanism 104, within the scope of the present invention, any suitable shape may be integrated to the housing of the transmitter unit 101 so as to effectively be opened and closed to respectively expose and seal off the sensor introducer trigger mechanism 104 as desired by the patient. For example, the circular opening on the transmitter unit 101 may alternatively be formed in an oblong shape, a triangular shape, a rectangular shape, and so on.

Figure 5A:
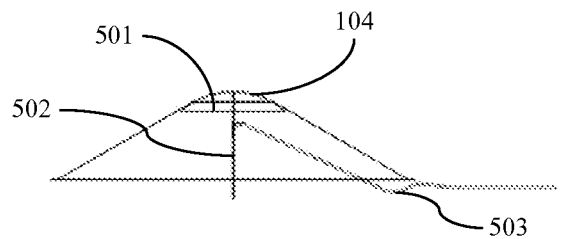
FIGS. 5A-5B illustrate a side view and a perspective view, respectively, of the sensor introducer trigger mechanism with the sensor positioned in the pre-deployment position in accordance with one embodiment of the present invention.
Figure 5B:
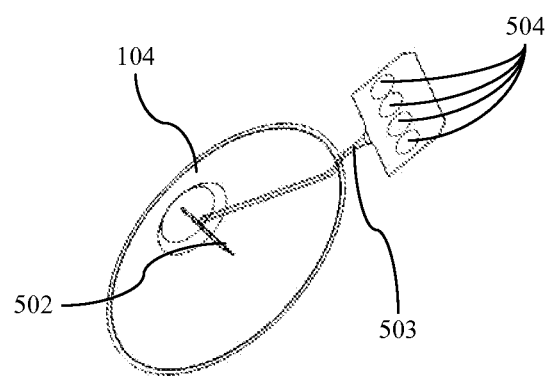

FIGS. 5A-5B illustrate a side view and a perspective view, respectively, of the sensor introducer trigger mechanism with the sensor positioned in the pre-deployment position in accordance with one embodiment of the present invention. Referring to FIGS. 5A and 5B, as can be seen, the sensor introducer trigger mechanism 104 in one embodiment includes a trigger portion 501 operatively coupled to an introducer portion 502. As shown, the trigger portion 501 of the sensor introducer trigger mechanism 104 is configured to displace the introducer portion 502 in a substantially skin-inserting direction, e.g., a substantially vertical direction relative to the patient's skin surface. Further, as shown in the Figures, an analyte sensor 503 is provided in cooperation with the introducer portion 502 such that in one embodiment, when the trigger portion 501 is activated by the patient, for example, by the application of downward pressure on the outer surface of the trigger portion (the outer surface of the "dome shaped" area), the introducer portion 502 is in turn configured to be driven in a substantially complimentary direction to the direction of the applied pressure, and further, displacing at least a portion of the sensor 503 with the introducer portion 502. In other words, the introducer portion 502 is configured in one embodiment to transcutaneously place a portion of the sensor 503 so that the portion of the sensor is in fluid contact with the biological fluid (for example, interstitial fluid) of the patient.

Referring to FIGS. 5A-5B, the sensor 503 is in one embodiment also provided with one or more contact points 504 which are configured to be in electrical contact with the corresponding electrical contacts of the transmitter unit 101. That is, in the case of analyte sensors, the working, reference, and counter electrodes (in certain embodiments an electrode may function as both reference and counter electrodes) are each coupled to a respective one of the contact points 504, and in turn, each of which are in electrical communication with the respective contacts on the transmitter unit 101.

In this manner, in one embodiment, the sensor detected analyte levels are provided to the transmitter unit 101, for example, as current signals, and which are in turn, converted to respective digital signals for transmission (including, for example, RF transmission) to a receiver unit for further data processing and data analysis (including drug (e.g., insulin) therapy management, infusion control, and health monitoring and treatment, for example). That is, the monitored analyte data may be used by the patient and/or the patient's healthcare provider to modify the patient's therapy such as an infusion protocol (such as basal profile modifications in the case of diabetics) as necessary to improve insulin infusion therapy for diabetics, and further, to analyze trends in analyte levels for better treatment.

While glucose is described as an example of the detected and/or monitored analyte, within the scope of the present invention, analytes that may be detected or monitored also include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be detected and/or monitored.

Figure 6:
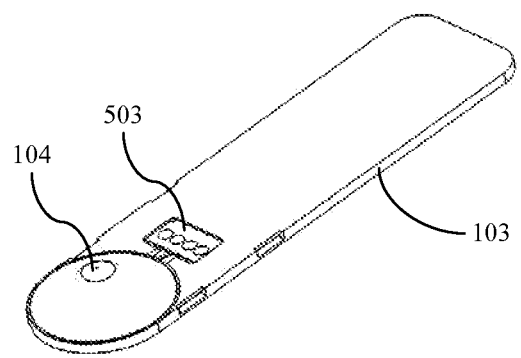
FIG. 6 illustrates a perspective view of the sensor introducer trigger mechanism and the transmitter unit base portion in cooperation with the sensor in pre-deployment position in accordance with one embodiment of the present invention.

FIG. 6 illustrates a perspective view of the sensor introducer trigger mechanism and the transmitter unit base portion in cooperation with the sensor in pre-deployment position in accordance with one embodiment of the present invention. As shown, the one or more contact points 504 of the sensor 503 (which in one embodiment may correspond to a respective one of the working electrode, a counter electrode, and a reference electrode, for example), are configured to couple to a respective contact on the transmitter unit 101 (FIGS. 3A-3B) such that the sensor 503, which is in fluid contact with the patient's biological fluids, is in electrical communication with the transmitter unit 101.

Furthermore, as can be seen from FIG. 6, the substantially dome shaped inserter introducer trigger mechanism 104 is configured to be collapsible when the patient applies downward pressure to drive the introducer portion 502 through the patient's skin. Further, when the downward pressure is removed from the dome shaped inserter introducer trigger mechanism 104, the outer inserter introducer trigger mechanism 104 is configured to return to substantially the original shape, and concurrent therewith, removing the introducer portion 502 from the insertion site of the patient, while leaving behind the subcutaneous portion of the sensor in fluid contact with the patient's biological fluid. This can also be seen with FIGS. 7A-7B as described below.

Figure 7A:
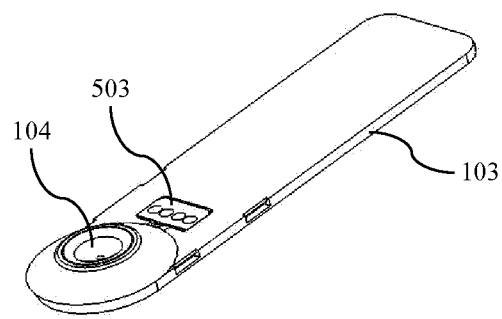
FIG. 7A illustrates a perspective view of the sensor introducer trigger mechanism and the transmitter unit base portion in post deployment position in accordance with one embodiment of the present invention.
Figure 7B:
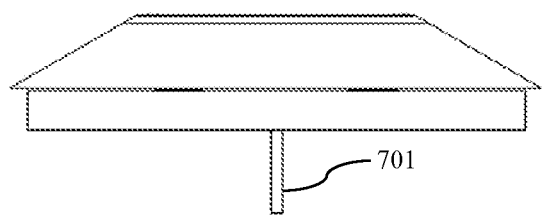
FIG. 7B illustrates a side view of the sensor introducer trigger mechanism in post sensor deployment position in accordance with one embodiment of the present invention.

FIG. 7A illustrates a perspective view of the sensor introducer trigger mechanism and the transmitter unit base portion in post deployment position, and FIG. 7B illustrates a side view of the sensor introducer trigger mechanism in post sensor deployment position in accordance with one embodiment of the present invention. More specifically, it can be seen from FIGS. 7A-7B that when the downward pressure is applied upon the substantially dome shaped inserter introducer trigger mechanism 104, the upper conical portion of the inserter introducer trigger mechanism 104 takes a substantially inverted conical shape, and with the same force, driving the portion 701 of the sensor 503 (FIG. 5A) through the patient's skin. In one embodiment, the inserter introducer trigger mechanism 104 may be made of one of stainless steel, rubber, polyester, or PET film, or any other suitable material that is flexible and provides the properties described herein, including being reversibly collapsible.

Figure 8A:
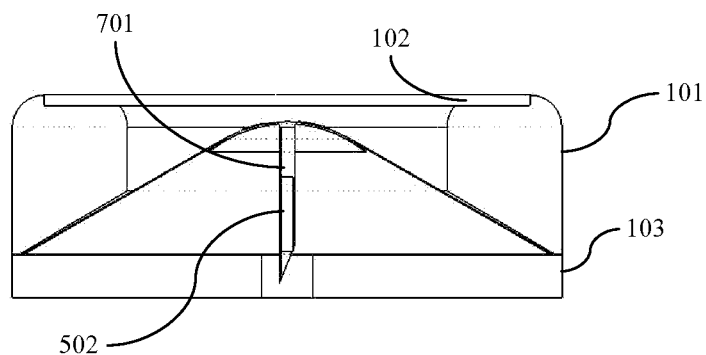
FIG. 8A is a cross sectional view of the sensor introducer trigger mechanism before the sensor insertion in accordance with one embodiment of the present invention.
Figure 8B:
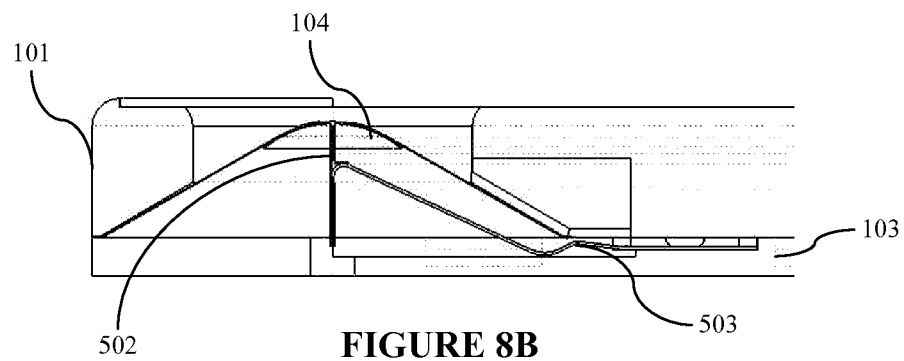
FIG. 8B is a cross sectional side view of the sensor introducer trigger mechanism before the sensor insertion in accordance with one embodiment of the present invention.

FIG. 8A is a cross sectional view of the sensor introducer trigger mechanism 104 before the sensor insertion, and FIG. 8B is a cross sectional side view of the sensor introducer trigger mechanism 104 before the sensor insertion in accordance with one embodiment of the present invention. As can be seen from FIG. 8A, the portion 701 of the sensor 503 is substantially retained in cooperation with the introducer portion 502 (e.g., a microneedle), all of which are substantially retained within the integrated inserter introducer and transmitter assembly 100 (FIGS. 1A-1B).

Moreover, referring to FIG. 8B, the non-transcutaneously displaced portion of the sensor 503 is also substantially completely retained within the integrated inserter introducer and transmitter assembly 100. That is, in one embodiment of the present invention, the transmitter unit 101 as well as the sensor insertion mechanism (e.g., sensor introducer trigger mechanism 104) are provided within a single integrated housing. Furthermore, as discussed in additional detail below, after the deployment of the sensor 503 transcutaneously so as to have a portion 701 thereof in fluid contact with the patient's biological fluid, the sensor insertion mechanism is retained within the integrated housing itself, so that the patient is not required to further handle the sharp and contaminated needle portion of the sensor introducer assembly.

Figure 9A:
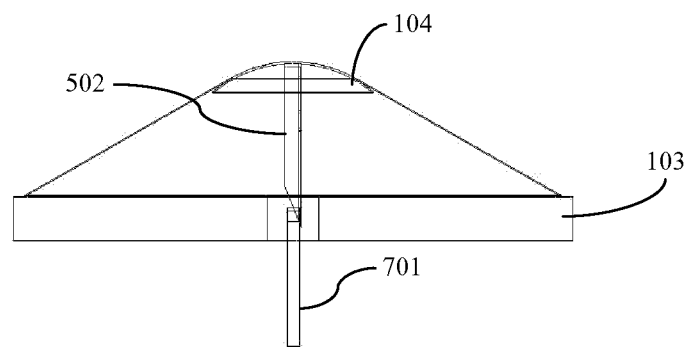
FIGS. 9A and 9B are cross sectional views of the sensor introducer trigger mechanism after sensor insertion and withdrawal of the introducer for retention within the integrated sensor introducer and transmitter assembly in accordance with one embodiment of the present invention.
Figure 9B:
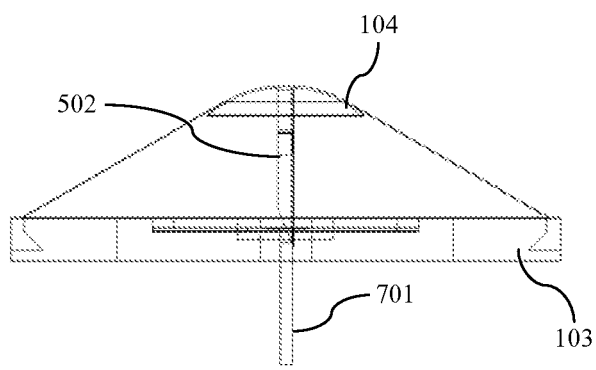

FIGS. 9A and 9B are cross sectional views of the sensor introducer trigger mechanism 104 after sensor insertion and withdrawal of the introducer for retention within the integrated sensor introducer and transmitter assembly in accordance with one embodiment of the present invention. Referring to FIGS. 9A-9B, it can be seen that after the sensor 503 is placed transcutaneously through the patient's skin at the intended location and in fluid contact with the patient's biological fluid, the introducer portion 502 is retained substantially completely within the dome shaped sensor introducer trigger mechanism 104 provided within the integrated sensor introducer and transmitter assembly 100.

Furthermore, while the sensor 503 is described as substantially transcutaneously placed in the patient, within the scope of the present invention, the sensor may be wholly implantable under the skin of the patient, or at least a portion of the sensor may be provided under the skin of the patient so as to be in fluid contact with the patient's interstitial fluid.

In one embodiment, the introducer portion 502 is configured to be retained within the assembly 100 during the entire duration of the sensor 503 in operation for monitoring the patient's analyte levels, and is discarded along with the sensor 503 after use. In this manner, while the transmitter unit 101 may be reusable, in one embodiment of the present invention, the base portion 103 and the sensor introducer trigger mechanism 104 along with the sensor 503 are discarded after each use.

Further, the detected analyte signals from the sensor 503 may be provided to transmitter unit 101, which is, in one embodiment, configured to wirelessly or otherwise transmit data corresponding to the detected analyte levels from the sensor 503 to a receiver unit, where the receiver unit may include an analyte, e.g., glucose, monitor unit and/or an insulin pump unit and/or a computer terminal and/or any other electronic device capable of being configured for wireless communication. A physical connection may be provided in certain embodiments.

Within the scope of the present invention, the receiver unit functions may be integrated into portable electronic devices such as a watch, a pager, a mobile telephone, and a personal digital assistant. Additional information on the detection, monitoring and analysis of analyte levels are described in further detail in U.S. Pat. No. 6,175,752 entitled "Analyte Monitoring Device and Methods of Use" the disclosure of which is incorporated herein by reference for all purposes. In certain embodiments, the transmitter may also be capable of wirelessly or otherwise receiving a signal from a receiver such that a receiver may also be capable of transmitting information to the transmitter.

In a further embodiment, the transmitter unit 101 may include a wireless communication unit for wireless transmission of the signal, where the wireless communication unit may include one or more of a radio frequency (RF) communication unit, a Bluetooth® communication unit, an infrared communication unit, an 801.11x communication unit, or a Zigbee communication unit. Similarly, the receiver unit may be configured to support one or more of the above-referenced wireless communication protocols to communicate with the transmitter unit.

In the manner described above, an apparatus including an integrated sensor insertion unit includes a base unit, a sensor coupled to the base unit, and an insertion unit disposed on the base unit, the insertion unit operatively coupled to the sensor and configured to place at least a portion of the sensor under a skin of a patient, wherein the insertion unit is configured to remain disposed on the base unit after sensor placement.

In one embodiment, a transmitter unit may be disposed on the base unit, where the transmitter unit is configured to operatively couple to the sensor. Also, the transmitter unit may include an opening portion configured to substantially cover the insertion unit when the transmitter unit is disposed on the base unit, where the opening portion is slidably disposed on the transmitter unit to selectively expose the insertion unit. Further, the opening portion may be alternately pivotally mounted to the transmitter unit to selectively expose the insertion unit.

Additionally the base unit, the sensor, and the insertion unit in one embodiment may be formed as an integrated disposable unit.

In a further embodiment, the insertion unit may include a sharp portion, the sharp portion configured to couple to a portion of the sensor, the sharp portion further configured to pierce through a skin of the patient to position at least the portion of the sensor in the patient, where at least the portion of the sensor may be configured to be in fluid contact with a biological fluid of a patient. In one embodiment, the biological fluid includes one of interstitial fluid or blood.

In an additional embodiment, the sensor is an analyte sensor, which includes a glucose sensor.

An apparatus in still a further embodiment of the present invention includes a transmitter mount, a sensor coupled to the transmitter mount, the sensor configured to be in fluid contact with a biological fluid of a patient, and a sensor introducer coupled to the sensor and configured to place at least a portion of the sensor under the skin of the patient, the sensor introducer integrated with the transmitter mount such that the sensor introducer is retained with the transmitter mount after sensor placement.

Also provided in still a further embodiment, is an adhesive layer where the transmitter mount disposed on the adhesive layer, and a transmitter unit coupled to the transmitter mount on the adhesive layer, where the transmitter unit further configured to be in electrical communication with the sensor.

The adhesive layer in one embodiment is positioned substantially around a sensor insertion location on the skin of the patient.

Moreover, the transmitter unit may include an opening portion, the opening portion configured to selectively provide access to the sensor introducer.

Further, the transmitter unit in yet another embodiment may be configured to transmit one or more signals corresponding to a respective one or more sensor signals, where the one or more sensor signals may correspond to or are associated with a respective one or more of analyte levels detected by the sensor.

The one or more analyte levels may include one of a glucose level, a lactate level, or an oxygen level.

In addition, in a further embodiment, there may be provided a receiver unit configured to receive the one or more signals from the transmitter unit.

A method in yet still another embodiment includes the steps of placing at least a portion of a sensor under the skin of a patient, substantially covering the sensor introducer mechanism, and discarding the sensor introducer mechanism with the sensor.

An analyte detection apparatus for use with an analyte sensor in still another embodiment includes a transmitter, and an analyte sensor insertion unit operatively coupled to the transmitter.

A system in accordance with still another embodiment includes a transmitter mount, a sensor coupled to the transmitter mount, the sensor configured to be in fluid contact with a biological fluid of a patient, a sensor introducer coupled to the sensor and configured to place at least a portion of the sensor under the skin of the patient, the sensor introducer integrated with the transmitter mount such that the sensor introducer is retained with the transmitter mount after sensor placement, and a transmitter unit coupled to the transmitter mount, the transmitter unit electrically coupled to the sensor, and configured to transmit one or more signals associated with the biological fluid levels of the patient.

An insertion kit in one embodiment of the present invention includes a base unit, a sensor coupled to the base unit, and an insertion unit disposed on the base unit, the insertion unit operatively coupled to the sensor and configured to place at least a portion of the sensor under a skin of a patient, the insertion unit including a sensor introducer, wherein the sensor introducer is retained substantially disposed on the base unit after sensor placement.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus, comprising:
a housing;
an analyte sensor disposed in the housing; and
an insertion unit disposed in the housing, the insertion unit operatively coupled to the sensor and configured to place at least a portion of the sensor under a skin layer, wherein the insertion unit is configured to remain disposed in the housing after sensor placement;
wherein the insertion unit includes a compressible introducer mechanism coupled to an introducer, the compressible introducer mechanism configured to displace at least a portion of the sensor and the introducer through the skin layer to an insertion position under the skin layer;
wherein the compressible introducer mechanism moves from a non-compressed state to a compressed state in response to a manual force applied to the compressible introducer mechanism, wherein when the compressible introducer mechanism moves from the non-compressed state to the compressed state, the at least the portion of the sensor and the introducer are inserted through the skin layer to the insertion position;
wherein removal of the manual force from the compressible introducer mechanism causes the compressible introducer mechanism to move from the compressed state to the non-compressed state and automatically withdraw the at least the portion of the introducer from under the skin layer while retaining the at least the portion of the sensor at the insertion position; and further
wherein the compressible introducer mechanism is contained within the housing when the compressible introducer mechanism is in the non-compressed state and the compressed state.

2. The apparatus of claim 1 further including sensor electronics operatively coupled to the analyte sensor.

3. The apparatus of claim 1 wherein the insertion unit includes a sharp portion, the sharp portion configured to couple to the at least the portion of the analyte sensor, the sharp portion further configured to pierce through the skin layer to position the at least the portion of the analyte sensor at the insertion position.

4. The apparatus of claim 1 wherein the at least the portion of the analyte sensor is configured for fluid contact with a biological fluid under the skin layer.

5. The apparatus of claim 4 wherein the biological fluid includes one of interstitial fluid or blood.

6. The apparatus of claim 1 wherein the analyte sensor is a glucose sensor.

7. An apparatus, comprising:
a housing;
a sensor coupled to the housing, the sensor configured to be in fluid contact with a biological fluid under a skin layer;
sensor electronics coupled to the housing and in electrical communication with the sensor; and
a sensor introducer coupled to the sensor and the housing, and configured to place at least a portion of the sensor under the skin layer, the sensor introducer including a compressible introducer mechanism to displace at least a portion of the sensor and the sensor introducer through the skin layer to an insertion position under the skin layer;
wherein the compressible introducer mechanism moves from a non-compressed state to a compressed state in response to a manual force applied to the introducer mechanism, wherein when the compressible introducer mechanism moves from the non-compressed state to the compressed state, the at least the portion of the sensor and the sensor introducer are inserted through the skin layer to the insertion position;
wherein removal of the manual force from the compressible introducer mechanism causes the compressible introducer mechanism to move from the compressed state to the non-compressed state and automatically withdraw the at least the portion of the sensor introducer from the insertion position under the skin layer while retaining the at least the portion of the sensor at the insertion position under the skin layer; and further
wherein the compressible introducer mechanism is contained within the housing when the compressible introducer mechanism is in the non-compressed state and the compressed state.

8. The apparatus of claim 7 wherein the sensor electronics includes an opening portion, the opening portion configured to selectively provide access to the sensor introducer.

9. The apparatus of claim 8 wherein the sensor electronics is configured to communicate one or more signals corresponding to a respective one or more sensor signals.

10. The apparatus of claim 9 wherein the one or more sensor signals correspond to a respective one or more of analyte levels monitored by the sensor.

11. The apparatus of claim 10 wherein the one or more analyte levels include one of a glucose level, a lactate level, or an oxygen level.

12. The apparatus of claim 7 wherein the biological fluid of a patient includes one of interstitial fluid or blood.

13. An apparatus, comprising:
a housing;
an analyte sensor disposed in the housing;
a sensor introducer disposed in the housing and detachably coupled to the analyte sensor; and
a compressible introducer mechanism disposed in the housing and operatively coupled to the sensor and the sensor introducer, the compressible introducer mechanism configured to place at least a portion of the sensor and the sensor introducer under a skin layer to an insertion position;

wherein the compressible introducer mechanism moves from a non-compressed state to a compressed state in response to a manual force applied to the compressible introducer mechanism, wherein when the compressible introducer mechanism moves from the non-compressed state to the compressed state, the at least the portion of the sensor and the sensor introducer are inserted through the skin layer to the insertion position;

wherein removal of the manual force from the compressible introducer mechanism causes the compressible introducer mechanism to move from the compressed state to the non-compressed state and automatically withdraw the at least the portion of the introducer from under the skin layer while retaining the at least the portion of the sensor at the insertion position; and further wherein the compressible introducer mechanism is contained within the housing when the compressible introducer mechanism is in the non-compressed state and the compressed state.

14. The apparatus of claim 13 further including sensor electronics operatively coupled to the analyte sensor.

15. The apparatus of claim 14 wherein the sensor electronics includes an opening configured to provide access to the sensor introducer.

16. The apparatus of claim 14 wherein the sensor electronics is configured to communicate one or more signals corresponding to a respective one or more sensor signals.

17. The apparatus of claim 16 wherein the one or more sensor signals correspond to a respective one or more of analyte levels monitored by the sensor.

18. The apparatus of claim 17 wherein the one or more analyte levels include one of a glucose level, a lactate level, or an oxygen level.

19. The apparatus of claim 13 wherein the at least the portion of the analyte sensor is configured for fluid contact with a biological fluid under the skin layer.

20. The apparatus of claim 19 wherein the biological fluid includes one of interstitial fluid or blood.

* * * * *